(12) United States Patent
Elimelech et al.

(10) Patent No.: US 10,835,296 B2
(45) Date of Patent: Nov. 17, 2020

(54) SPINOUS PROCESS CLAMP

(71) Applicant: Augmedics Ltd., Yokneam Illit (IL)

(72) Inventors: Nissan Elimelech, Beerotaim (IL); Daniel Messinger, Migdal Haemek (IL); Stuart Wolf, Yokneam (IL)

(73) Assignee: AUGMEDICS LTD., Yokneam Illit (IL)

( * ) Notice: Subject to any disclaimer, the term of this patent is extended or adjusted under 35 U.S.C. 154(b) by 0 days.

(21) Appl. No.: 16/120,480

(22) Filed: Sep. 4, 2018

(65) Prior Publication Data

US 2019/0175228 A1 Jun. 13, 2019

Related U.S. Application Data

(60) Provisional application No. 62/595,598, filed on Dec. 7, 2017.

(51) Int. Cl.
*A61B 17/70* (2006.01)
*A61B 34/20* (2016.01)
(Continued)

(52) U.S. Cl.
CPC ........ *A61B 17/7067* (2013.01); *A61B 17/122* (2013.01); *A61B 17/1227* (2013.01);
(Continued)

(58) Field of Classification Search
CPC .............. A61B 17/7067; A61B 17/122; A61B 17/1227; A61B 2017/00367; A61B 2017/00477; A61B 34/10; A61B 34/20; A61B 2014/2057; A61B 2014/2072; A61B 90/39; A61B 2090/363; A61B 2090/3916
(Continued)

(56) References Cited

U.S. PATENT DOCUMENTS 3,101,715 A * 8/1963 Glassman ............ A61B 17/282
606/207
4,711,512 A 12/1987 Upatnieks
(Continued)

FOREIGN PATENT DOCUMENTS

EP 3247297 A1 11/2017

OTHER PUBLICATIONS

European Application # 18192544.7 search report dated Apr. 2, 2019.

*Primary Examiner* — Pedro Philogene
(74) *Attorney, Agent, or Firm* — Kligler & Associates Patent Attorneys Ltd

(57) ABSTRACT

Apparatus, consisting of a hinge, defining a hinge axis, and a pair of opposing jaws terminating at respective proximal regions and distal regions. The proximal regions are connected to the hinge so that at least one of the jaws is configured to rotate about the hinge between a closed state and an open state of the jaws. In addition, the jaws are curved in respective planes parallel to the hinge axis, and terminate in respective narrowed ends at the respective distal regions, wherein in the closed state the jaws are configured to grip one or more sections of vertebrae. The apparatus also has a support structure that is configured to retain the hinge and the pair of opposing jaws. A multiplicity of sharp teeth are disposed on respective inner surfaces of the opposing jaws.

20 Claims, 12 Drawing Sheets

(51) Int. Cl.
   *A61B 17/122* (2006.01)
   *A61B 34/10* (2016.01)
   *A61B 90/00* (2016.01)
   *A61B 17/00* (2006.01)

(52) U.S. Cl.
   CPC .............. *A61B 34/10* (2016.02); *A61B 34/20* (2016.02); *A61B 90/39* (2016.02); *A61B 2017/00367* (2013.01); *A61B 2017/00477* (2013.01); *A61B 2034/2057* (2016.02); *A61B 2034/2072* (2016.02); *A61B 2090/363* (2016.02); *A61B 2090/3916* (2016.02)

(58) Field of Classification Search
   USPC ................... 606/246–279; 623/17.11–17.16
   See application file for complete search history.

(56) References Cited

U.S. PATENT DOCUMENTS

| | | | |
|---|---|---|---|
| 4,944,739 A * | 7/1990 | Torre | A61B 17/2812 606/207 |
| 5,147,365 A * | 9/1992 | Whitlock | A61B 17/158 606/88 |
| 5,665,092 A | 9/1997 | Mangiardi et al. | |
| 6,675,040 B1 * | 1/2004 | Cosman | G06T 3/00 600/427 |
| 6,847,336 B1 | 1/2005 | Lemelson et al. | |
| 7,107,091 B2 | 9/2006 | Jutras et al. | |
| 7,235,076 B2 | 6/2007 | Pacheco | |
| 7,239,330 B2 | 7/2007 | Sauer et al. | |
| 7,241,292 B2 * | 7/2007 | Hooven | A61B 18/1445 606/41 |
| 7,627,085 B2 | 12/2009 | Boyden et al. | |
| 8,271,069 B2 | 9/2012 | Jascob et al. | |
| 8,737,708 B2 | 5/2014 | Hartmann et al. | |
| 8,784,450 B2 | 7/2014 | Moskowitz et al. | |
| 8,908,952 B2 | 12/2014 | Isaacs et al. | |
| 8,922,589 B2 | 12/2014 | Laor | |
| 8,941,559 B2 | 1/2015 | Bar-Zeev et al. | |
| 9,005,211 B2 | 4/2015 | Brundobler et al. | |
| 9,011,441 B2 | 4/2015 | Bertagnoli et al. | |
| 9,060,757 B2 | 6/2015 | Lawson et al. | |
| 9,084,635 B2 | 7/2015 | Nuckley et al. | |
| 9,123,155 B2 | 9/2015 | Cunningham et al. | |
| 9,294,222 B2 * | 3/2016 | Proctor, Jr. | H03M 13/03 |
| 9,928,629 B2 | 3/2018 | Benishti et al. | |
| 2004/0019263 A1 * | 1/2004 | Jutras | A61B 90/39 600/407 |
| 2008/0221625 A1 * | 9/2008 | Hufner | A61B 17/1757 606/324 |
| 2008/0253527 A1 | 10/2008 | Boyden et al. | |
| 2009/0062869 A1 | 3/2009 | Claverie et al. | |
| 2011/0248064 A1 * | 10/2011 | Marczyk | A61B 17/07207 227/114 |
| 2011/0306873 A1 | 12/2011 | Shenai et al. | |
| 2015/0084990 A1 | 3/2015 | Laor | |
| 2015/0277123 A1 | 10/2015 | Chaum et al. | |
| 2015/0282735 A1 | 10/2015 | Rossner | |
| 2015/0310668 A1 | 10/2015 | Ellerbrock | |
| 2015/0350517 A1 | 12/2015 | Duret et al. | |
| 2016/0022287 A1 | 1/2016 | Nehls | |
| 2016/0030131 A1 | 2/2016 | Yang et al. | |
| 2016/0086380 A1 | 3/2016 | Vayser et al. | |
| 2016/0191887 A1 | 6/2016 | Casas | |
| 2016/0249989 A1 | 9/2016 | Devam et al. | |
| 2016/0324580 A1 | 11/2016 | Esterberg | |

* cited by examiner

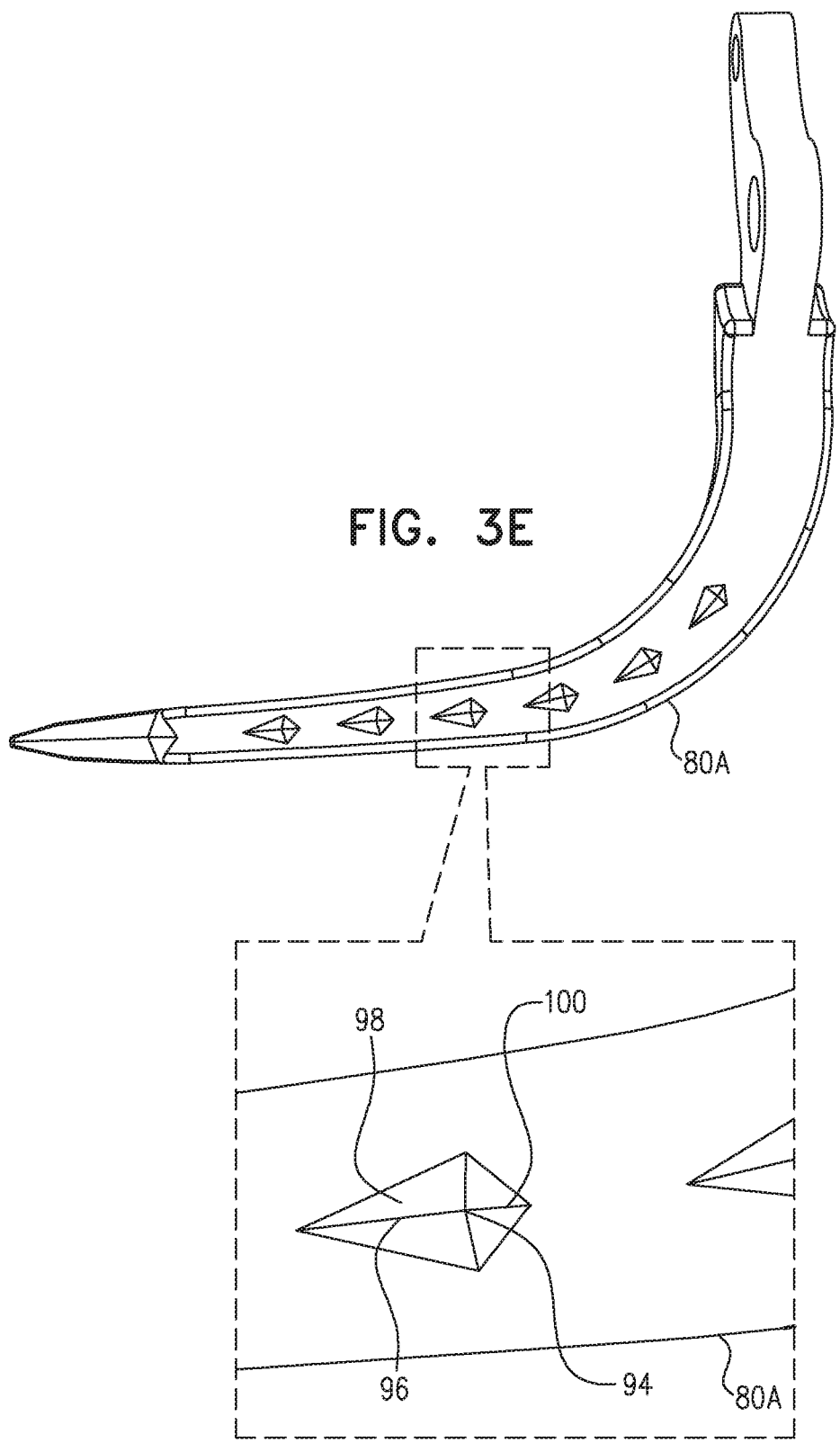

SPINOUS PROCESS CLAMP

CROSS-REFERENCE TO RELATED APPLICATIONS

This application claims the benefit of U.S. Provisional Patent Application 62/595,598, filed 7 Dec. 2017, which is incorporated herein by reference.

FIELD OF THE INVENTION

The present invention relates generally to clamps, and particularly to clamps that may be attached to the spine of a living subject.

BACKGROUND OF THE INVENTION

During image guided surgery, it may be important to register elements of a patient, upon whom the surgery is being performed, with equipment generating the image. This is typically the case where the surgery comprises a surgical navigation system, which generates images of portions of the patient that are in registration with the actual portions. Some prior art references that may be used in image guided surgery are provided below.

U.S. Pat. No. 5,665,092 to Mangiardi et al., describes a marker for surgical procedures which permits an operating surgeon to mark the place to be operated on accurately in a manner which is as free of pain as possible for the patient.

U.S. Pat. No. 7,107,091 to Jutras et al., describes a surgical device, adapted for use with an image guided surgical system, that is stated to facilitate monitoring interdependently mobile bone elements.

U.S. Pat. No. 8,271,069 to Jascob et al., describes a surgical navigation system for navigating a region of a patient that may include a non-invasive dynamic reference frame and/or fiducial marker, sensor tipped instruments, and isolator circuits. The dynamic reference frame may be placed on the patient in a precise location for guiding the instruments.

U.S. Pat. No. 8,737,708 to Hartmann et al., states that a patient defines a patient space in which an instrument can be tracked and navigated. An image space is defined by image data that can be registered to the patient space. A tracking device can be connected to a member in a known manner that includes imageable portions that generate image points in the image data. Selected image slices or portions can be used to register reconstructed image data to the patient space.

U.S. Pat. No. 8,784,450 to Moskowitz et al., describes thoracic/lumbar and cervical spinous process staples which staple/fuse adjacent spinous processes.

U.S. Pat. No. 9,005,211 to Brundobler et al., describes a method for positioning a guide tube fixation device at a spinal structure of a patient. The method includes attaching an attachment element to the spinal structure, attaching a guide tube to the attachment element, wherein the guide tube is calibrated prior to attachment, and navigating a part of the guide tube to a predetermined location relative to a target region of the patient.

U.S. Pat. No. 9,011,441 to Bertagnoli et al., describes a method for preparing an interspinous space to receive an implantable device.

U.S. Pat. No. 9,060,757 to Lawson et al., describes an instrument for distracting and/or compressing adjacent vertebrae. The instrument includes a yoke, a first blade movably mounted to the yoke, a second blade mounted to the yoke and an adjustment system.

U.S. Pat. No. 9,084,635 to Nuckley et al., describes a number of spinal stabilization devices for aligning and fixing vertebrae during surgery, e.g. to facilitate accurate placement of pedicle screws. One stabilization device includes a pair of spiked rails biased to clamp shut and thereby passively engage a number of vertebrae.

U.S. Patent Application 2015/0282735 to Rossner describes a device and method for a surgical navigation system comprising a connection unit, a marker carrier unit removably attached to the connection unit, and an attachment unit connected to the connection unit for fixing the device to a body part of a patient.

U.S. Patent Application 2016/0022287 to Nehls describes temporary, radiographically opaque, bone markers having first and second penetration members that are concentric with one another and are configured to pierce bone.

SUMMARY OF THE INVENTION

An embodiment of the present invention provides apparatus, including:

a hinge, defining a hinge axis;

a pair of opposing jaws terminating at respective proximal regions and distal regions, wherein the proximal regions are connected to the hinge so that at least one of the jaws is configured to rotate about the hinge between a closed state and an open state of the jaws, and the jaws are curved in respective planes parallel to the hinge axis, and terminate in respective narrowed ends at the respective distal regions, wherein in the closed state the jaws are configured to grip one or more sections of vertebrae;

a support structure, configured to retain the hinge and the pair of opposing jaws; and a multiplicity of sharp teeth disposed on respective inner surfaces of the opposing jaws.

In a disclosed embodiment the pair of opposing jaws includes a jaw fixed with respect to the hinge, the apparatus further having a verification point located in a fixed position within an element of the apparatus consisting of one of the fixed jaw and the support structure, wherein the verification point is identifiable in a fluoroscopic image of the element.

In a further disclosed embodiment the apparatus includes a detachable positioning marker, configured to be fixedly and rigidly attached in one of a plurality of positions to the support structure. The apparatus may also include a surgical navigation system, an image capturing device therein, and a processor, wherein the surgical navigation system is remote from the positioning marker, and wherein the image capturing device is configured to capture an image of the marker and wherein the processor is configured to analyze the image so as determine the position and orientation of the marker in a frame of reference defined by the system.

In a yet further disclosed embodiment each of the sharp teeth has a pyramid-like configuration. Each of the sharp teeth may terminate in a sharp point. Alternatively or additionally, each of the sharp teeth may have a proximally-facing sharp edge. Further alternatively or additionally, each of the sharp teeth may have a distally-facing sharp edge.

In an alternative embodiment the respective proximal regions and distal regions consist of straight regions connected by a curved intermediate section. An angle between the straight sections may be in a range from 70°-90°.

In a further alternative embodiment the respective narrowed ends are rounded and truncated.

In a yet further alternative embodiment the jaws are configured so that when the jaws grip the one or more sections of the vertebrae the jaws bend so that respective distal terminations of the distal regions deflect by up to 1 mm.

Typically, the support structure includes a lever mechanism attached to the proximal region of the at least one of the jaws, the mechanism having a first configuration fixedly maintaining the jaws in the open state, and a second configuration fixedly maintaining the jaws in the closed state.

There is further provided, according to an embodiment of the present invention, a method, consisting of:

providing a clamp, including:

a hinge, defining a hinge axis;

a pair of opposing jaws, each jaw terminating at respective proximal regions and distal regions, wherein the proximal regions are connected to the hinge so that at least one of the jaws is configured to rotate about the hinge between a closed state and an open state of the jaws, and the jaws are curved in respective planes parallel to the hinge axis, and terminate in respective narrowed regions at the respective distal regions, wherein in the closed state the jaws are configured to grip one or more sections of vertebrae;

a support structure, configured to retain the hinge and the pair of opposing jaws;

a multiplicity of sharp teeth disposed on respective inner surfaces of the opposing jaws; and a detachable positioning marker, configured to be fixedly and rigidly attached in one of a plurality of positions to the support structure; and using the clamp during an image guided surgery procedure.

The present invention will be more fully understood from the following detailed description of the embodiments thereof, taken together with the drawings in which:

BRIEF DESCRIPTION OF THE DRAWING

FIGS. 3A, 3B, 3C, 3D and 3E are schematic figures illustrating selected elements of the clamp, according to an embodiment of the present invention;

DETAILED DESCRIPTION OF EMBODIMENTS

Overview

Embodiments of the present invention provide apparatus that may be used as a clamp, typically a spinous process clamp that, in contrast to prior art clamps, has two curved jaws. By curving the jaws, the clamp is able to fasten onto two or more spinous processes of a patient, and yet may be inserted into the patient through a relatively small incision.

A hinge connects the two jaws, and at least one jaw rotates about the hinge. The hinge defines a hinge axis, and each jaw is curved in a respective plane parallel to the hinge axis. In addition, each jaw terminates in a respective narrowed region, the narrowed regions facilitating insertion of the jaws of the clamp into the patient via the incision.

Each jaw is configured to have sharp teeth, which enable the clamp, when it is closed, to both cut into and effectively grip the spinous processes.

A clamp support structure retains the two jaws and the hinge. The support structure may be used to manipulate the jaws, after insertion of the jaws into the patient, so that the jaws grip one or more spinous processes of the patient, while the support structure remains external to the patient.

Once the jaws have gripped the spinous processes of the patient, the support structure of the clamp provides a rigid platform to which may be attached a positioning marker that does not move relative to the patient's spine. The clamp with its attached marker may be used during an image guided surgery procedure, in which a professional performing the procedure uses a surgical navigation system.

The surgical navigation system may find the position and orientation of the marker, and thus of the clamp, in a frame of reference of the system. Thus any relative movement between the patient and the system, which may be caused by movement of the patient and/or of the professional, may be compensated for.

The clamp may comprise a verification point, which is configured to be visible when illuminated by visible light, as well as to be identifiable in a fluoroscopic image of the clamp. As is described in more detail below, the professional using the surgical navigation system is able to use the verification point to confirm, and if necessary adjust, different elements of the system in order to achieve correct registration of respective frames of reference of the elements.

DETAILED DESCRIPTION

In the following, all directional references (e.g., upper, lower, upward, downward, left, right, top, bottom, above, below, vertical, and horizontal) are only used for identification purposes to aid the reader's understanding of the present invention, and do not create limitations, particularly as to the position, orientation, or use of embodiments of the invention.

Figure 1:
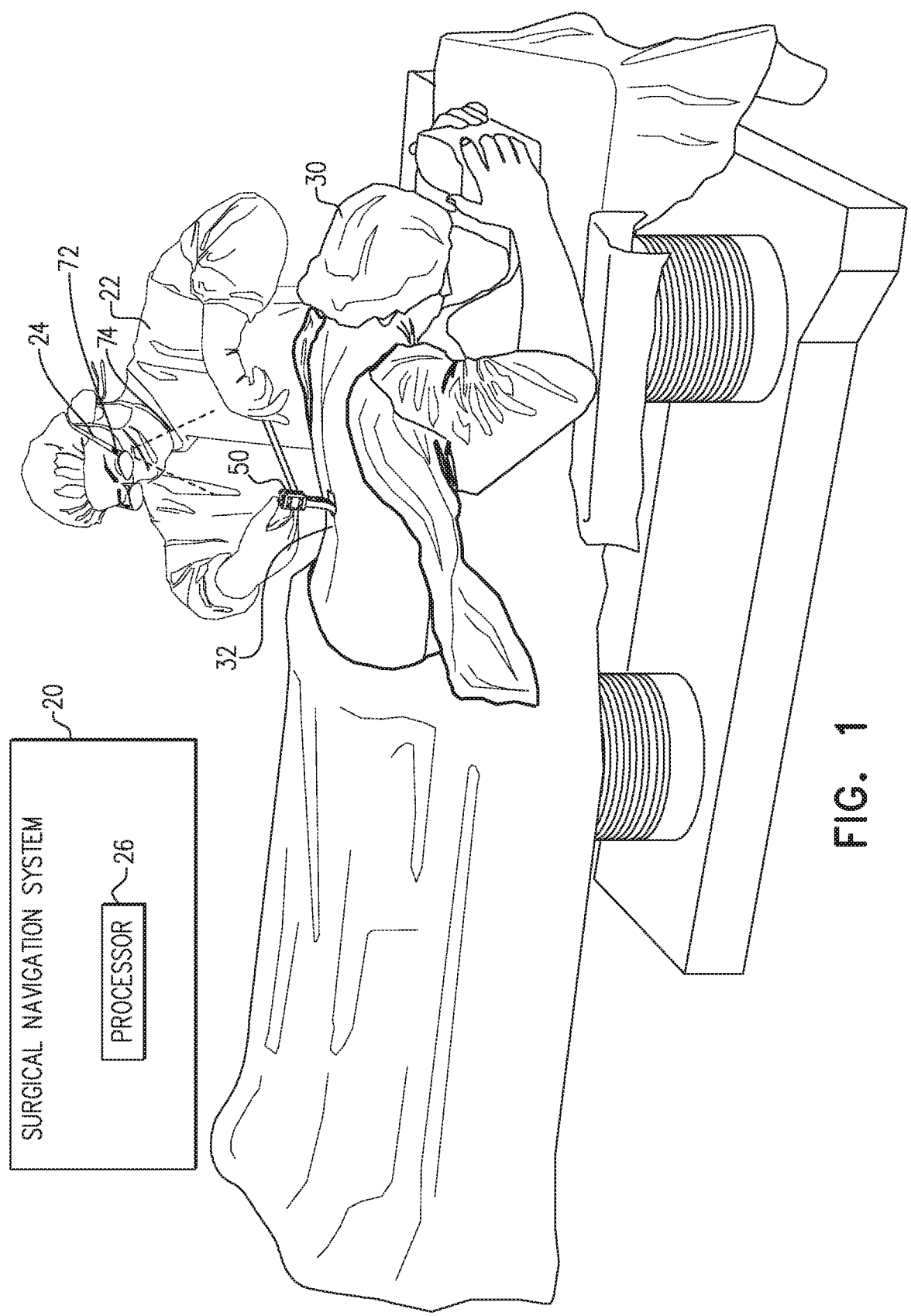
FIG. 1 is a schematic illustration of a medical procedure, according to an embodiment of the present invention.

Reference is now made to FIG. 1, which is a schematic illustration of a medical procedure, according to an embodiment of the present invention. During the procedure, performed by a professional 22, the professional uses a surgical navigation system 20, which assists the professional in performance of the procedure. Surgical navigation system 20 comprises a processor 26, which operates elements of the system, and which communicates with an augmented reality assembly 24, worn by professional 22, that is incorporated in the system. Assembly 24 comprises, inter alia, an image capturing device 72, also termed herein a camera 72, that has a field of view 74 and that is configured to capture images in the visible spectrum. Functions of system 20, processor 26, and device 72 are described below. An assembly similar to augmented reality assembly 24, and its operation, are described in U.S. Pat. No. 9,928,629, to Benishti, et al., whose disclosure is incorporated herein by reference.

The medical procedure exemplified here is performed on a patient 30, and during an initial stage of the procedure professional 22 makes an incision 32 into the patient's back. The professional then inserts a spinous process clamp 50 into the incision, so that opposing jaws of the clamp are located on opposite sides of the spinous processes. The professional then slides the clamp over the vertebral laminas, and adjusts the clamp to grip one or more spinous processes, selected by the professional, of the patient. As is described in more detail below, sharp edges of teeth on the jaws of the clamp face forward and are configured to cut muscles to the spinous processes, to facilitate insertion of the clamp. This enables lower sides of the jaws to slide on the vertebral laminas.

Figure 2A:
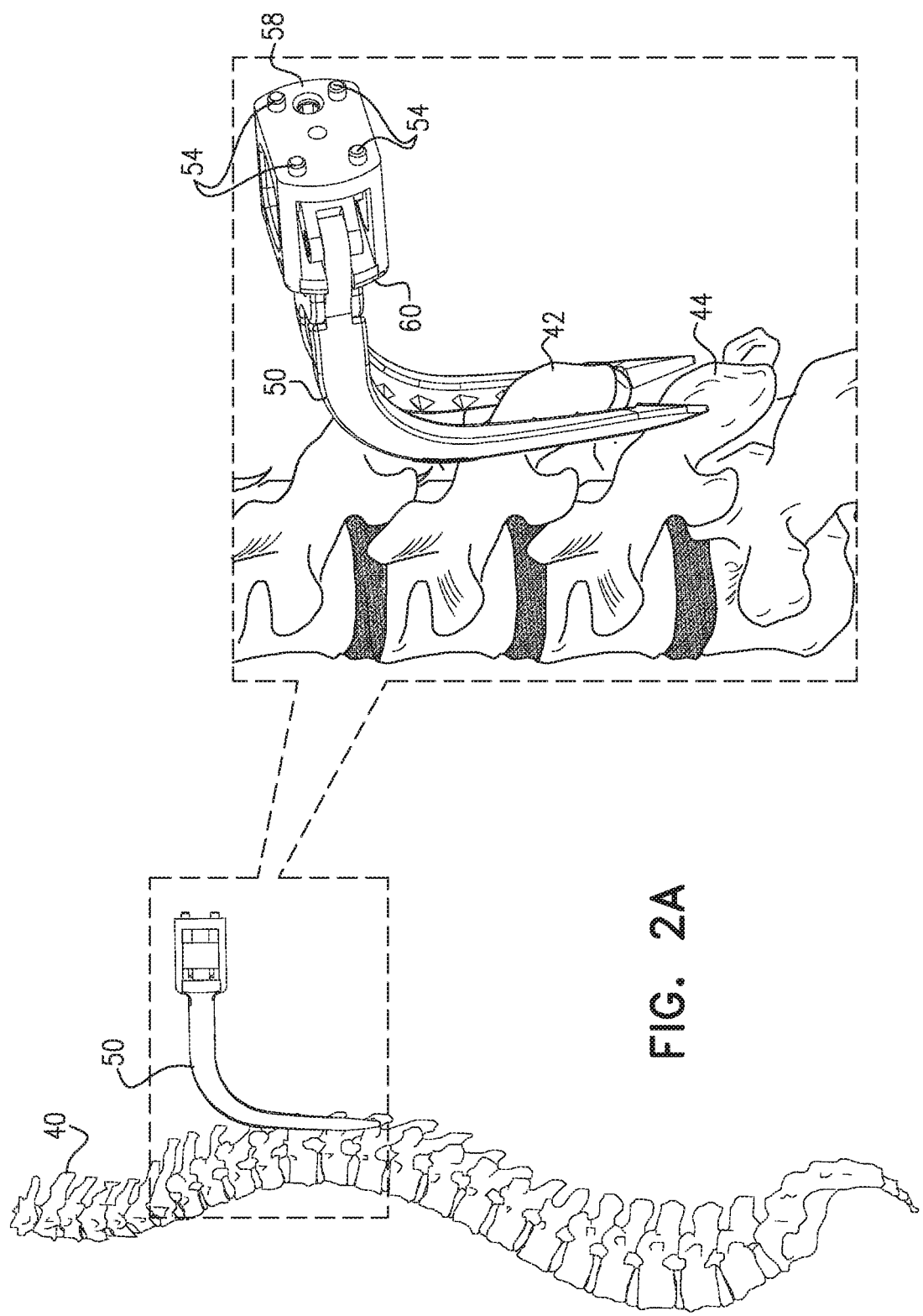
FIG. 2A schematically illustrates the situation after a clamp has been inserted and adjusted in the medical procedure, according to an embodiment of the present invention.

FIG. 2A schematically illustrates the situation after clamp 50 has been inserted and adjusted, according to an embodiment of the present invention. The figure illustrates that clamp 50 has been attached to grip a spine 40 of patient 30, and to specifically grip spinous processes 42 and 44 of vertebrae of the spine. As shown in FIG. 2A, clamp 50 comprises studs 54, herein by way of example there are four studs 54, protruding from a proximal surface 58 of a support structure 60 of the clamp.

Figure 2B:
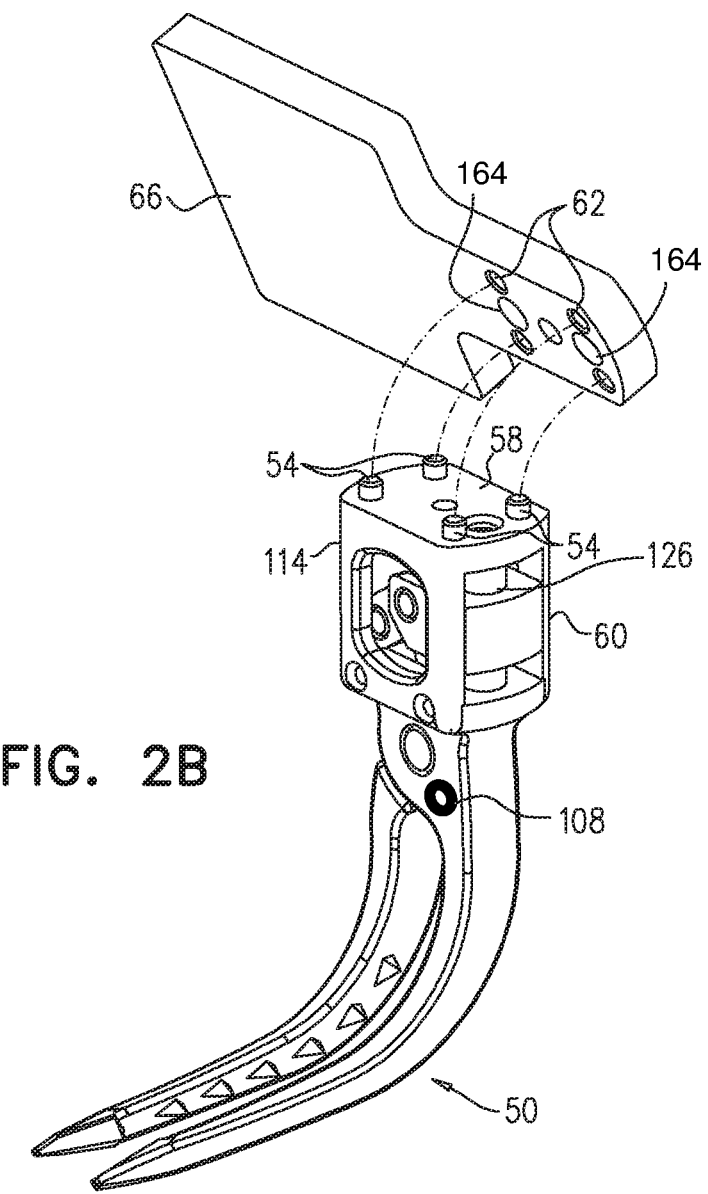
FIG. 2B schematically illustrates how a positioning marker is attached to the clamp, according to an embodiment of the present invention.

FIG. 2B schematically illustrates how a positioning marker 66 (shown in more detail in FIG. 2C) is attached to clamp 50, according to an embodiment of the present invention. As is explained below, marker 66 comprises radiopaque and optically visible elements that are in a known alignment with each other. Thus, a fluoroscopic image and an visible spectrum image of the marker may be used to register fluoroscopic and visible spectrum frames of reference of the marker, and of the clamp to which the marker is attached.

As is illustrated schematically in FIG. 2B, studs 54 of clamp 50 are configured to mate with apertures 62 of marker 66, so that when mated the marker is seated in one of a multiplicity of selectable positions on surface 58. In the embodiment described herein there are two selectable positions, and FIG. 2B illustrates the marker attached in one of those positions—to the left of the clamp (FIG. 5C shows the marker attached to the right of the clamp). However, it will be understood that the studs and apertures may be configured so that there are more than two selectable positions in which marker 66 may be seated on surface 58.

Figure 2C:
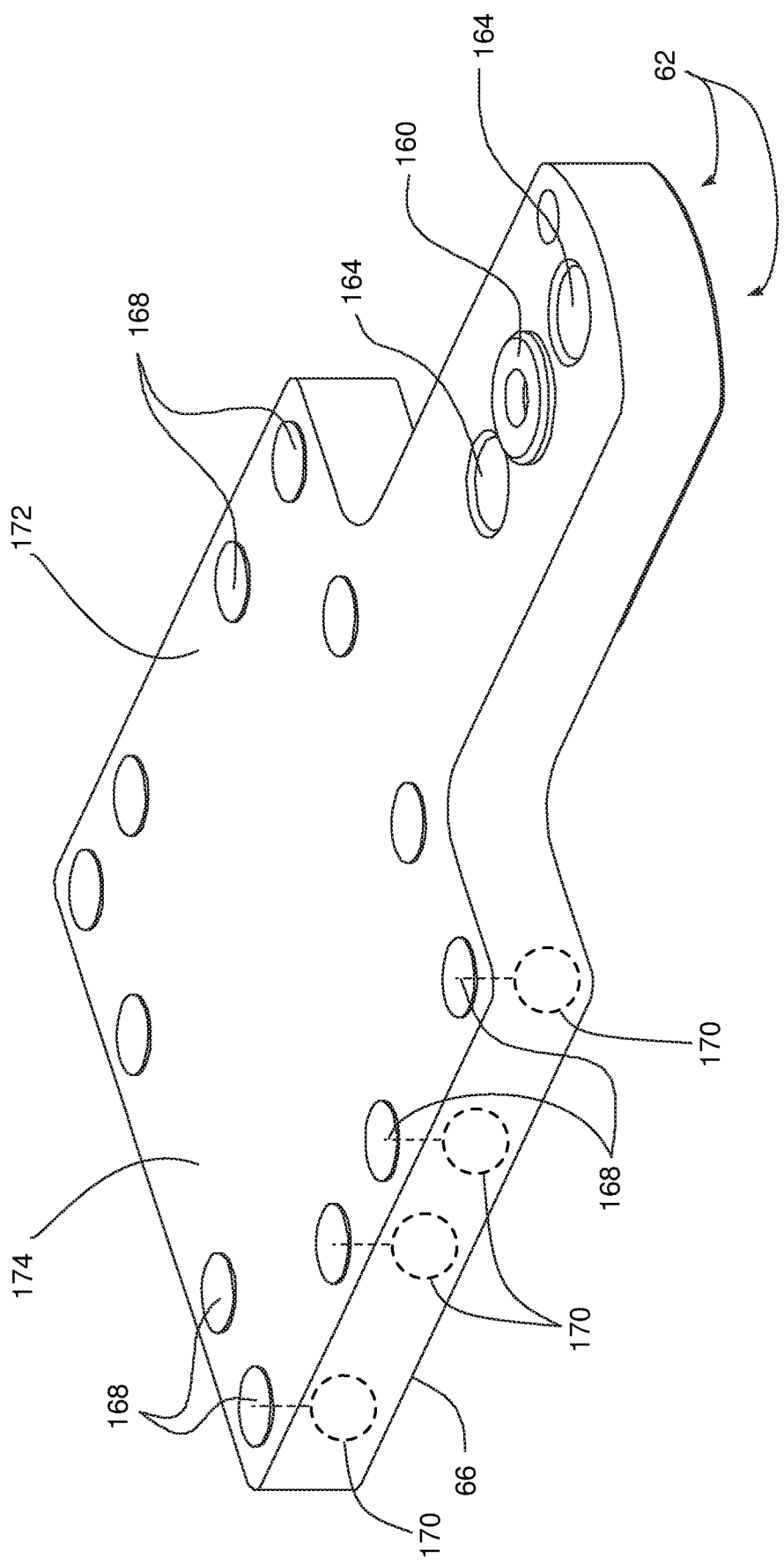
FIG. 2C schematically illustrates the positioning marker, according to an embodiment of the present invention.

FIG. 2C schematically illustrates details of marker 66, according to an embodiment of the present invention. Marker 66 is formed of a generally rectangular sold substrate 174, which comprises access holes 164 to a set screw 126 (described below with reference to FIG. 4B), and the holes are configured so that, regardless of the direction of attachment of the marker to the clamp, there is access to the set screw, via one of holes 164, after the marker has been attached.

During the procedure performed by professional 22, marker 66 is used as a fiduciary facilitating tracking of, and compensating for, any apparent movement of clamp 50 relative to assembly 24. The marker is also used to enable registration of a visible spectrum frame of reference of the marker with a CT frame of reference of the marker.

In order to act as a fiduciary, marker 66 comprises a multiplicity of reflectors 168 that are arranged on an upper face 172 of substrate 174 in a predetermined pattern. Reflectors 168 reflect visible light, and substrate 174 is typically opaque in the visible spectrum. When the reflectors are illuminated, by a projector (not shown) of surgical navigation system 20 and/or by ambient visible light, image capturing device 72 forms an image of the reflectors, and the image is transferred to processor 26.

To act as a registration device, marker 66 also comprises a multiplicity of radiopaque elements 170 that are arranged in a known predetermined physical relationship with respect to reflectors 168, and that are typically embedded in substrate 174. By way of example, elements 170 are assumed to be a preset distance directly below reflectors 168, and FIG. 2C shows four such elements as spheres. The material of substrate 174 is selected to be transparent under fluoroscopy.

In some embodiments reflectors 168 and radiopaque elements 170, rather than comprising separate entities as describe above, are comprised of combined single elements that are both reflective in visible light and radiopaque. For example, reflectors 168 may be formed from aluminum discs.

FIGS. 3A, 3B, 3C, 3D and 3E are schematic figures illustrating selected elements of clamp 50, according to an embodiment of the present invention. Clamp 50 comprises two opposing jaws 80A, 80B, which are connected, at proximal regions of the jaws, by a hinge pin 84. Jaws 80A, 80B are also herein termed jaws 80. At least one of the jaws is able to rotate around hinge pin 84, and in the figures jaw 80A is shown as rotating about the hinge pin, while jaw 80B is fixed with respect to the pin. The rotation enables jaws 80 to transfer in a continuous manner between an open state of the jaws, illustrated in FIG. 3A, and a closed state of the jaws, illustrated in FIG. 3B.

Figure 3A:
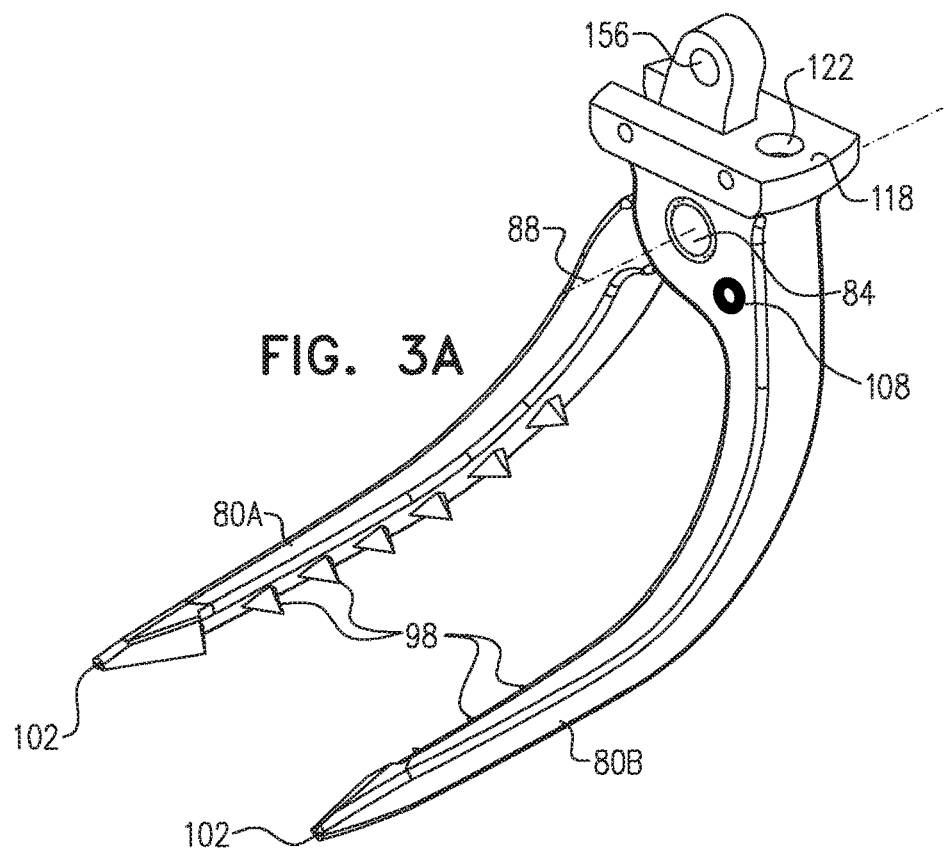
Figure 3B:
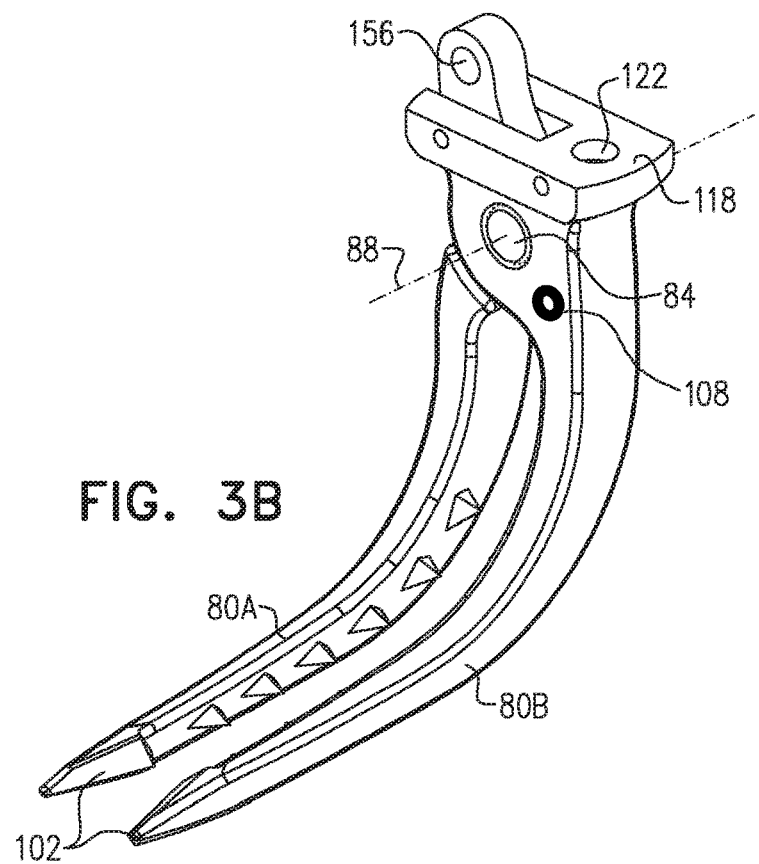
Figure 3C:
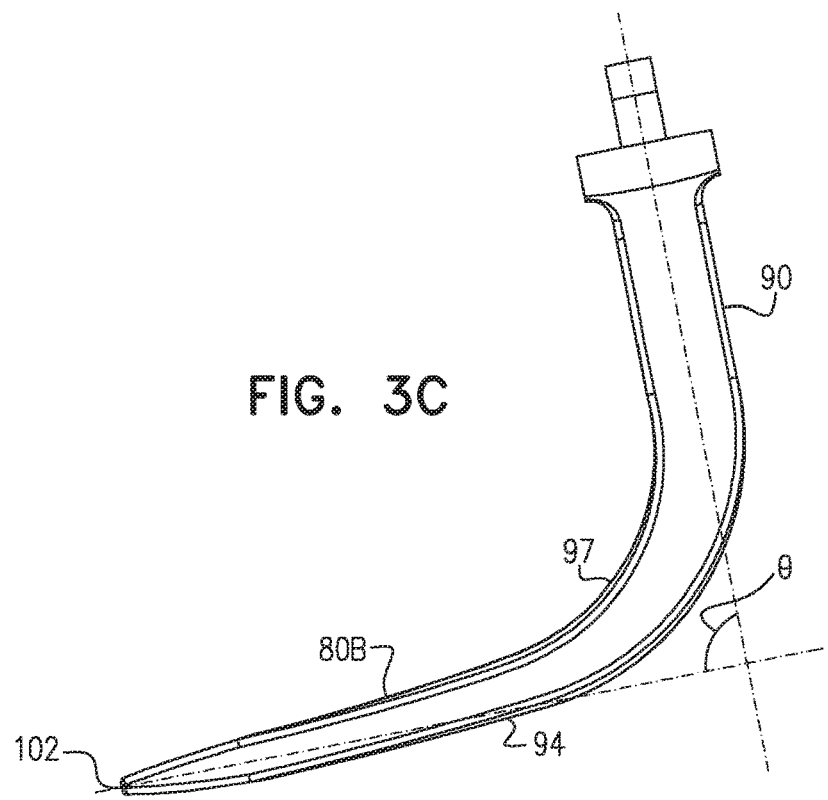

Hinge pin 84 defines a hinge axis 88, and each jaw 80 resides in a respective plane parallel to the hinge axis. FIG. 3C illustrates jaw 80B, and the figure has been drawn so that the plane of the paper of FIG. 3C corresponds to the plane wherein jaw 80B resides.

Each jaw 80 is curved within its respective plane. Thus, as illustrated in FIG. 3C, jaw 80B comprises a first substantially straight proximal region 90, a second substantially straight distal region 94, and a curved intermediate section 97 fixedly connecting the two straight regions. Proximal region 90 and distal region 94 are both terminating regions of the jaw 80B. Jaw 80A comprises two similar regions and a similar intermediate section that are connected as for jaw 80B. Typically, the distal regions of the jaws are sufficiently long so that they are able to simultaneously clamp on multiple adjacent spinous processes. In a disclosed embodiment the jaws are approximately 7 cm long.

In one embodiment an angle θ made by the intersection of the two straight sections is approximately 90°. However, in other embodiments, angle θ may be in the approximate range of 70°-90°.

Figure 3D:
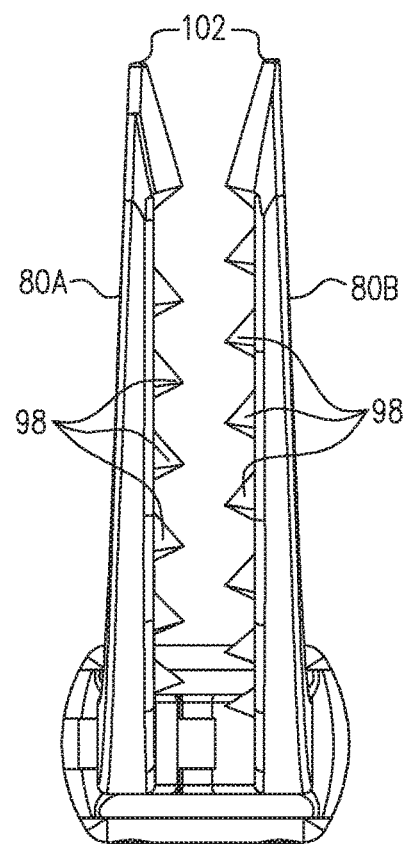

Typically each jaw 80 has a multiplicity of teeth 98 on an inner surface of the jaw, and the teeth of the two jaws are configured to be in opposition to each other. In one embodiment the opposing teeth are configured to intermesh with each other, as is illustrated in FIG. 3D, when the jaws are in their closed state.

In a disclosed embodiment the teeth have a pyramid-like shape, as illustrated in FIG. 3E, wherein the edges of the pyramid are sharp. In this case the pyramid of each tooth is configured to terminate in a sharp point 94, which facilitates the tooth gripping a spinous process.

In addition, for each tooth 98 one edge 96 of the pyramid is configured to be sharp and to face forward, so as to enable cutting of the muscles between the spinous processes when the clamp is inserted. Furthermore, another edge 100 of the pyramid of each tooth 98 is also configured to be sharp, but to face backward, so as to enable cutting of the muscles between the spinous processes on removal of the clamp. It will be understood that the forward-facing sharp edges of the pyramid-shaped teeth facilitate insertion of the clamp into patient 30, and that the backward-facing sharp edges of the pyramid-shaped teeth facilitate removal of the clamp from the patient.

Distal terminations 102 of each distal section of jaws 80A and 80B are narrowed by being slightly truncated and rounded, so that the distal tips of the jaws are not sharp. This configuration facilitates insertion of the clamp into soft body tissue, such as muscle or fat. In an alternative embodiment, edges 104 of internal faces 106 of terminations 102 are sharp so as also to facilitate penetration through tissue during insertion of the jaws.

In one embodiment jaws 80 are formed of anodized aluminum, typically black anodized aluminum for biocompatibility. In other embodiments jaws 80 may be formed of other metallic or non-metallic materials, including composites, having substantially the same physical properties as aluminum.

The proximal region of jaw 80B comprises a support structure retaining base 118 (FIGS. 3A, 3B) which in turn comprises a blind aperture 122. The functions of base 118 and aperture 122 are described below.

Clamp 50 also comprises a verification point 108 which is located in a known, predefined, fixed position on the clamp, and is herein assumed to be fixed, by way of example, to non-movable jaw 80B. However, verification point 108 may be located on other fixed portions of clamp 50, such as support structure 60.

Point 108 is situated on clamp 50 so that after the clamp has been inserted into patient 30, the verification point is visible to professional 22, when illuminated by visible light. In addition to being visible to professional 22, the verification point is configured to be identifiable, typically by image segmentation, in a fluoroscopic image, such as a computerized tomography (CT) image of clamp 50.

In order to be identifiable as described above, verification point 108 may comprise a protuberance and/or an indentation in jaw 80B, the protuberance and/or indentation being in the form of any convenient shape such as a cylinder. Alternatively or additionally, verification point 108 may be comprised of a material that is different from the material of clamp 50 wherein the point is located, so long as the material of the point is distinguishable in a fluoroscopic image, and also when viewed in visible light, from the material of the clamp. For example, if jaw 80B is formed from aluminum, point 108 may be formed from a titanium element, such as a spherical bead, that is inserted into the jaw, and that protrudes from the jaw. As another example, point 108 may comprise a void, such as a spherical air pocket, in jaw 80B, and the position of the point may be made visible by an optically visible marking, such as a paint spot, on a surface of the jaw above the void.

Other methods for forming verification point 108, including but not limited to combinations and subcombinations of those described herein, will be apparent to those having skill in the art, and all such methods are assumed to be comprised within the scope of the present invention.

Verification point is used by professional 22 to verify that different elements of system 20 are in registration, as is described in more detail below.

Figures 4A, 4B:
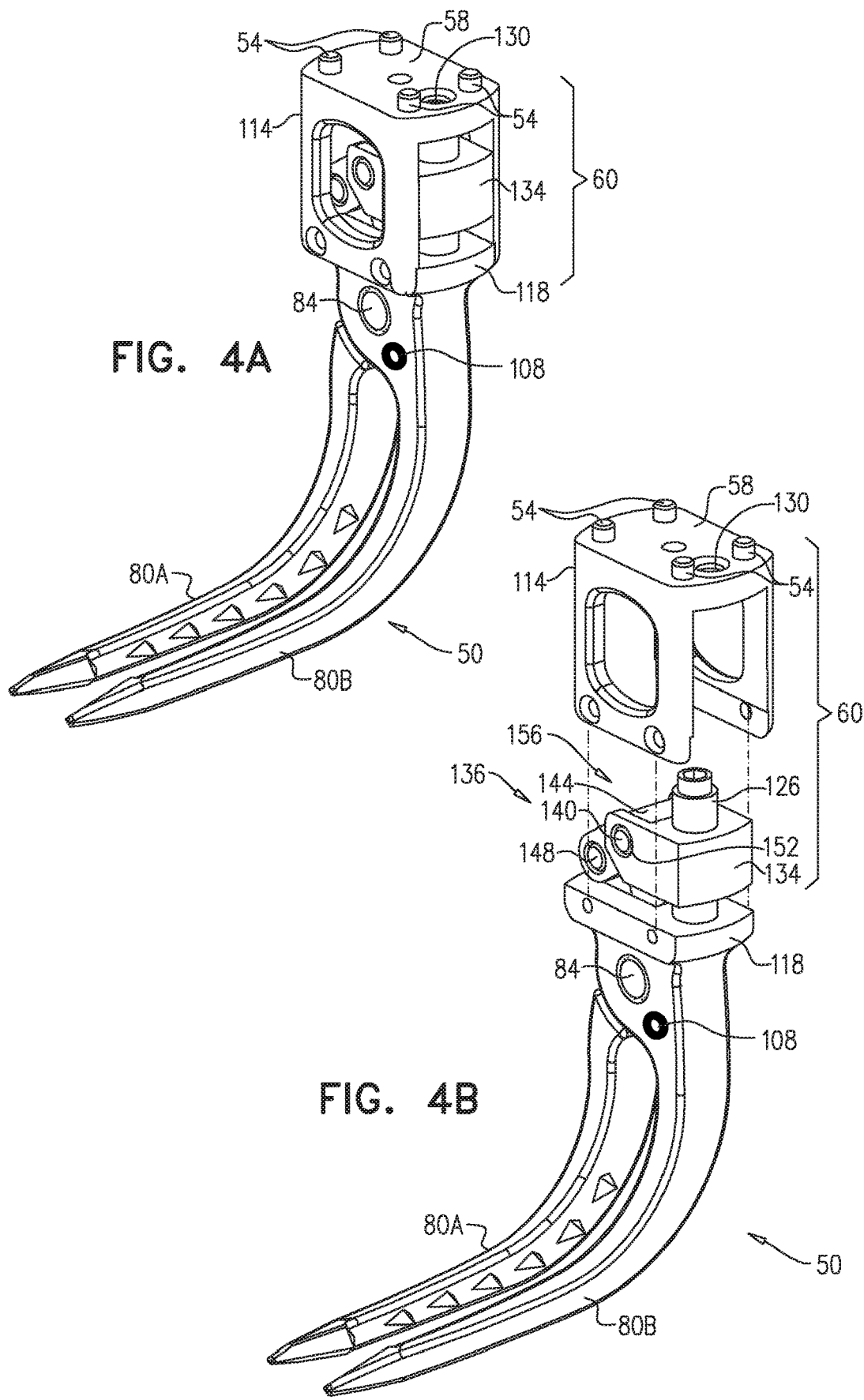
FIGS. 4A and 4B are schematic figures illustrating further elements of the clamp, according to an embodiment of the present invention.

FIGS. 4A and 4B are schematic figures illustrating further elements of clamp 50, according to an embodiment of the present invention. FIG. 4A illustrates the clamp when assembled, and shows support structure 60 which retains and activates jaws 80 and hinge 84. FIG. 4B illustrates support structure 60 with a cover 114 of the structure translated from other elements of the structure. Cover 114 is fixedly attached to support structure retaining base 118 (FIGS. 3A, 3B)

Support structure 60 contains a set screw 126 which is retained by, and rotates within, blind aperture 122 and an open aperture 130 in cover 114. Screw 126 has an external thread which mates with an internal thread of a nut 134, and sides of the nut touch and slide within walls of cover 114. Thus, rotating screw 126 translates nut 134 vertically within cover 114.

Nut 134 is connected by a lever mechanism 136 to jaw 80A. Mechanism 136 comprises a first hinge pin 140, a lever rod 144, and a second hinge pin 148. Rod 144 connects, at its proximal end, via first hinge pin 140, to an aperture 152 in nut 134, so that the rod is able to rotate around the first hinge pin. Rod 144 connects, at its distal end, via second hinge pin 148 to an aperture 156 in jaw 80A (aperture 156 is also shown in FIGS. 3A, 3B.)

Lever mechanism 136 is operated by rotating set screw 126. When the screw is rotated so that nut 134 has translated in an upper direction within structure 60, hinge 148 and aperture 156 are drawn towards the set screw, so that jaws 80 are in their open state, illustrated in FIG. 3A. When set screw 126 is rotated so that nut 134 has translated in a lower direction within structure 60, hinge 148 and aperture 156 move away from the set screw, so that jaws 80 are in their closed state, illustrated in FIG. 3B.

It will be understood that set screw 126, as it acts on lever mechanism 136, fixedly maintains jaws 80 in any desired configuration according to the rotation of the set screw. Thus a first rotation of screw 126 can fixedly maintain the jaws in an open state, and a second rotation can fixedly maintain the jaws in a closed state.

During the procedure referred to above, in their closed state the jaws typically grip one or more spinous processes. In order to firmly grip the processes in their closed state, in an embodiment the jaws are configured, by selection of the material of the jaws and by selection of the jaw dimensions, to bend so that respective distal terminations 102 of the jaws deflect by up to 1 mm from the jaw configuration when they are not gripping the processes. The deflection caused by the bending when the jaws grip spinous processes is illustrated schematically in FIG. 7.

From the descriptions of clamp 50 above, it will be appreciated that the combination of the narrowed distal sections of the jaws, their curved shape, and the relatively long length of the distal straight sections means that even with a small incision 32, clamp 50 can be manipulated to effectively grasp multiple spinous processes of patient 30.

Figure 5B:
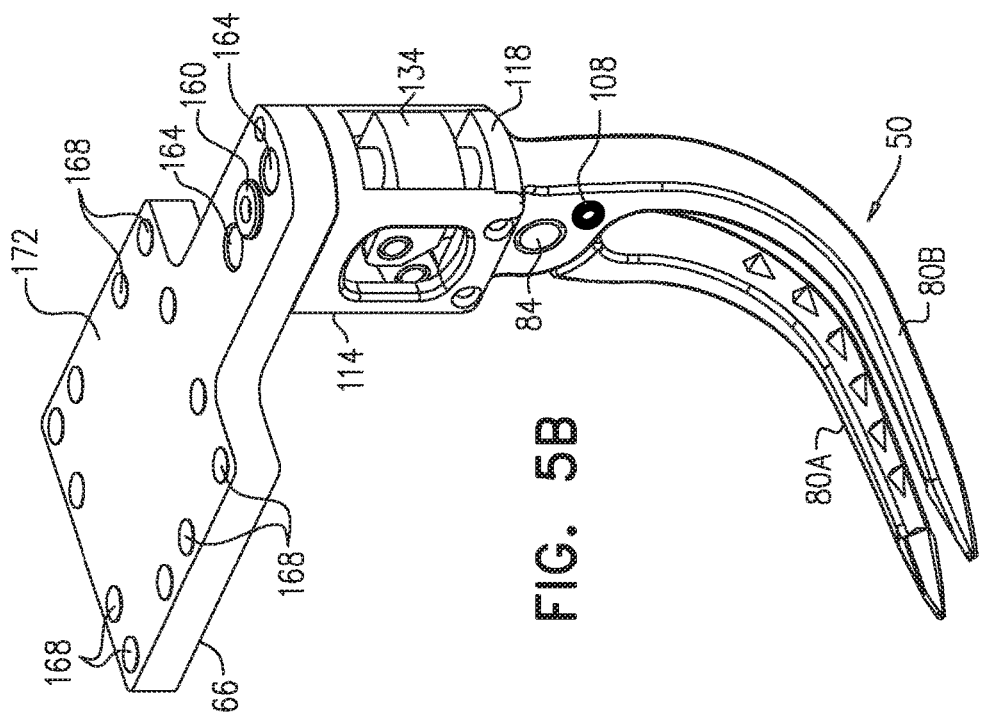
FIGS. 5A, 5B and 5C are schematic figures illustrating the attachment of the marker to the clamp, according to an embodiment of the present invention.
Figure 5A:
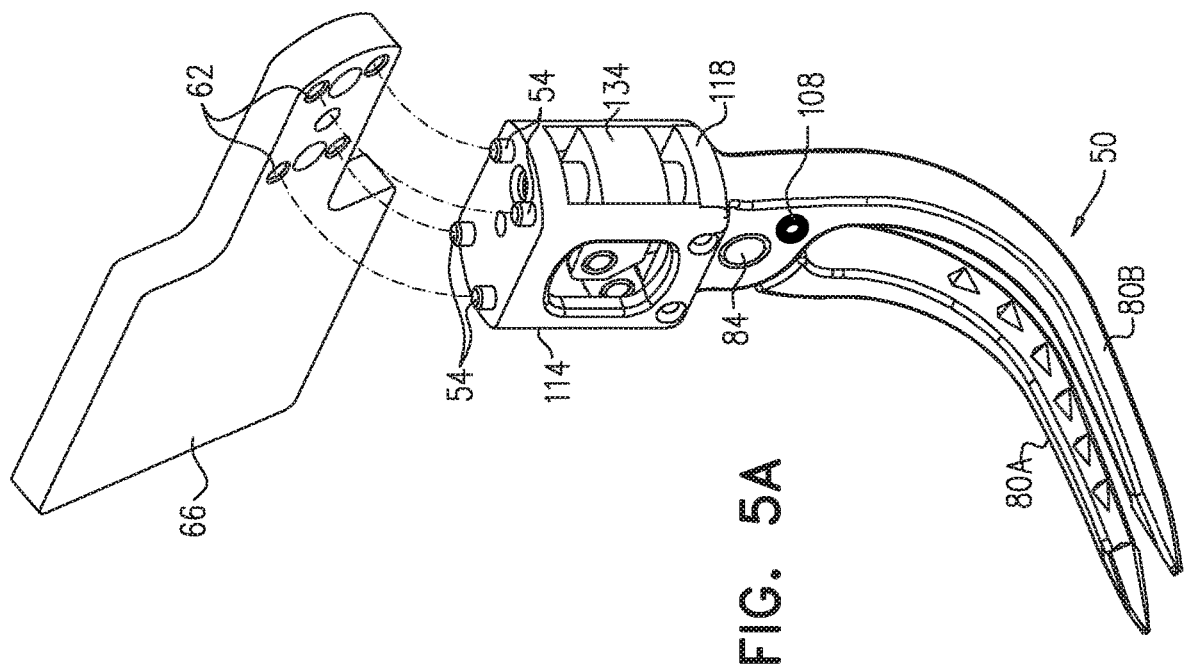
Figure 5C:
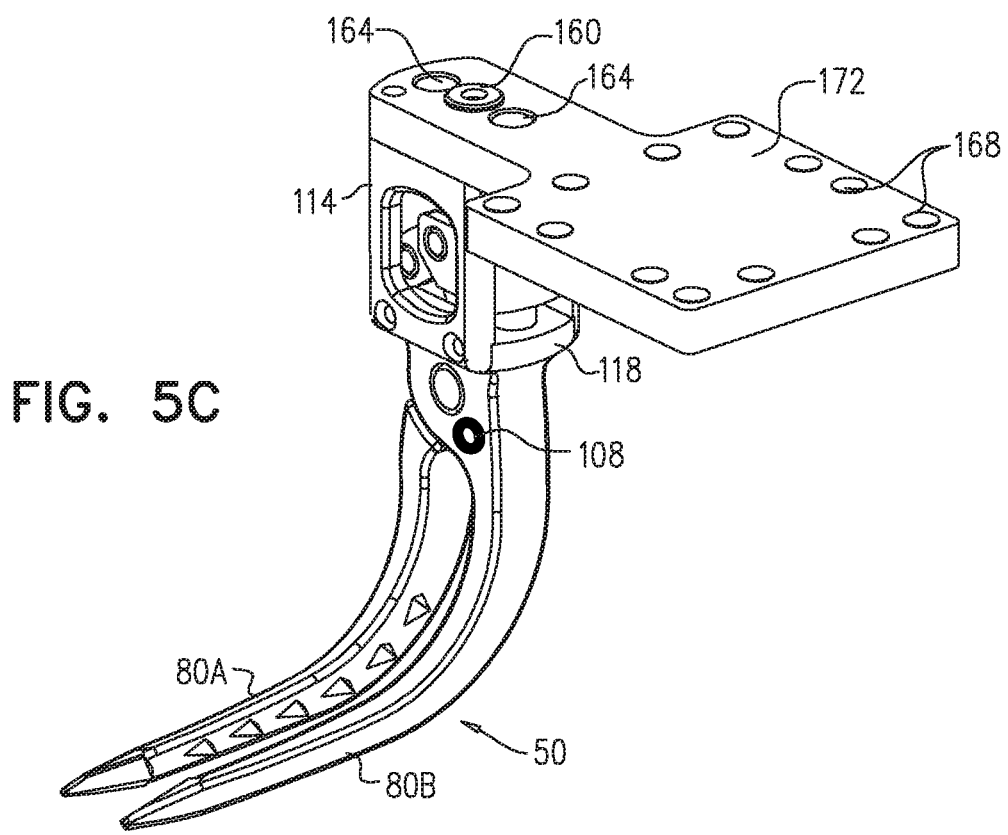

FIGS. 5A, 5B and 5C are schematic figures illustrating the attachment of marker 66 to clamp 50, according to an embodiment of the present invention. FIG. 5A illustrates apertures 62 of the marker mating with studs 54 of the clamp, and FIGS. 5B and 5C illustrate the marker and the clamp when they are attached. In the embodiment illustrated, marker 66 may be attached to clamp 50 so that the marker is to the left of the clamp, as shown in FIG. 5B, or to the right of the clamp, as shown in FIG. 5C. The marker is attached to the clamp with a screw 160.

During a procedure professional 22 can select which direction marker 66 is in so as to have best access to the patient. Typically, after insertion of jaws 80 into the patient, support structure 60 is approximately perpendicular to the patient's spine.

As is described above, marker 66 comprises access holes 164 to set screw 126, and the holes are configured so that, regardless of the direction of attachment of the marker to the clamp, there is access to the set screw, via one of holes 164, after the marker has been attached.

As is also described above, professional 22 may use surgical navigation system 20 (FIG. 1) during the procedure being performed on patient 30, and marker 66 may be used by the system as a fiduciary, enabling any relative movement between the patient and the system to be compensated for. In order to operate as a fiduciary, processor 26 of the surgical navigation system may use image capturing device 72 to recognize an image of the marker itself, or of optical elements such as reflectors 168 of the marker.

Thus, when reflectors 168 are illuminated by a projector (not shown) of surgical navigation system 20, and/or are illuminated by ambient visible light, image capturing device 72 forms an image of the reflectors, and the image is transferred to processor 26. Processor 26 uses the captured image to find the position and orientation of marker 66 and of clamp 50, and thus the position and orientation of the patient's spine, onto which clamp 50 is clamped, in a frame of reference defined by the system. Consequently, processor 26 is able to compensate for any relative movement between the marker and the system, which may be caused by movement of patient 30 and/or of professional 22, and the compensation enables the processor to adjust images presented to professional 22 so that the adjusted images appear stable with respect to the patient's spine.

Other methods for using marker 66, to compensate for any movement of patient 30, will be apparent to those having ordinary skill in the art, and all such methods are assumed to be comprised within the scope of the present invention.

Figure 6:
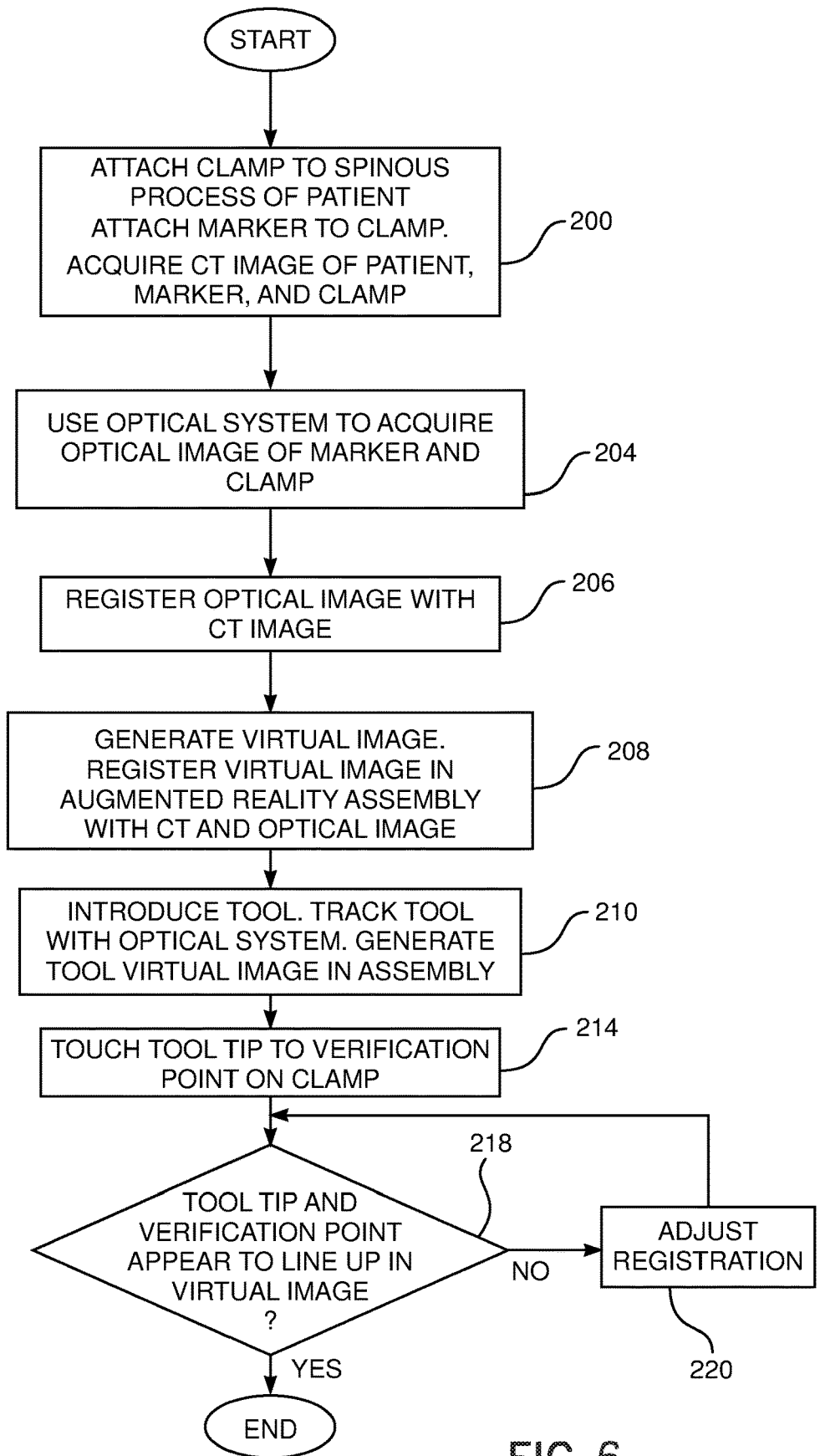
FIG. 6 is a flowchart of steps performed for the procedure of FIG. 1, according to an embodiment of the present invention.
Figure 7:
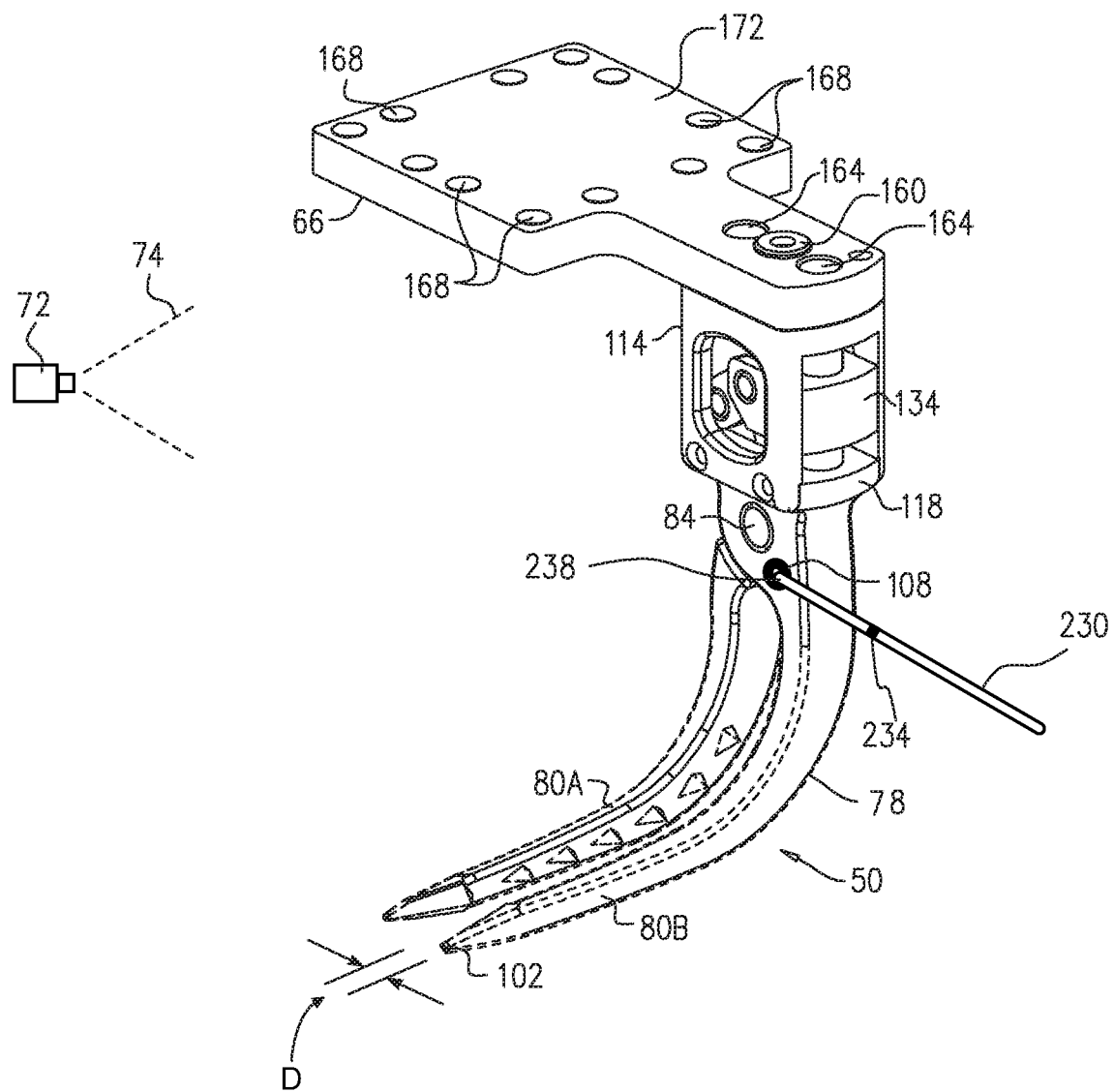
FIG. 7 is a schematic figure illustrating one of the steps of the flowchart, according to an embodiment of the present invention.

FIG. 6 is a flowchart of steps performed by professional 22 and processor 26 in operation of system 20, and FIG. 7 is a schematic figure illustrating one of the steps, according to an embodiment of the present invention. In an initial step 200 clamp 50 is inserted into patient 30 and is attached to one or more spinous processes of the patient, as is described above. Marker 66 is attached to clamp 50, as described above with reference to FIGS. 5A, 5B, 5C.

Once the clamp and marker are attached, a CT image of the patient, the clamp, and the marker is acquired, and processor 26 stores the image. The CT image includes a fluoroscopic image of verification point 108.

In an optical imaging step 204 the professional activates camera 72 to acquire an optical image of the marker, and processor 26 stores the optical image.

In a registration step 206, processor 26 registers a frame of reference defined by the CT image of marker 66 acquired in step 200 and a frame of reference defined by the optical image of marker 66 acquired in step 204 by methods which are well known in the art. It will be understood that the registration can be performed because reflectors 168, visible in the optical image, and radiopaque elements 170, visible in the CT image, are in a known physical relationship with respect to each other.

In a virtual image step 208, processor 26, using camera 72, generates a virtual image of the scene viewed by professional 22, herein assumed to comprise clamp 50, marker 66, and the spine of patient 30. The processor registers a frame of reference of the virtual image with the registered CT and optical frames of reference, and projects the registered virtual image in augmented reality assembly 24 so that it is visible to the professional.

The registrations produced in steps 206 and/or 208 may be inaccurate, and the following steps of the flowchart allow professional 22 to check on the accuracy of the registrations, and if necessary to correct the registrations.

FIG. 7 schematically illustrates clamp 50 inserted into patient 30, and a lower part 78 of the clamp that is within the patient is shown as drawn with broken lines. For simplicity the spinous processes of the patient are not shown in the figure. A deflection D, typically approximately 1 mm, of termination 102 of jaw 80B, caused by bending of the distal region of the jaw when it grips the spinous processes, is illustrated schematically in the figure. Jaw 80A will undergo a similar bending and termination deflection.

FIG. 7 also schematically illustrates camera 72 and field of view 74. It will be understood that the image formed by camera 72 includes images of the upper part of clamp 50 and marker 66, but does not include an image of lower part 78.

In a tool presentation step 210, professional 22 introduces a tool 230 (FIG. 7) into field of view 74 of camera 72. Tool 230 has one or more optical tracking elements 234 located in predefined positions on the tool, and the elements are configured so that an image of tool 230 and elements 234 produced by camera 72 enable processor 26 to track the position of a distal tip 238 of the tool.

The processor generates a virtual image of tool 230, and projects the tool virtual image in augmented reality assembly 24 so that it is visible to professional 26.

In a verification step 214, professional 26 touches distal tip 238 on verification point 108. This step may be performed with the virtual image produced by assembly 24 switched on or switched off.

In a decision step 218, the professional observes if the images of distal tip 238 and verification point 108 coincide. In an embodiment, the position of verification point 108, which is determined from the CT image acquired in step 200, is incorporated in the registered image being presented to the professional by assembly 24. Alternatively, rather than the professional checking for coincidence, processor 26 checks for coincidence.

If decision step 218 returns positive, i.e., the two images coincide, the registrations of the system described above are assumed successful, and the flowchart ends.

If decision step 218 returns negative, the registrations of steps 206 and/or 208 are not sufficiently correct, and control continues first to an adjust registration step 220, and from there to decision step 218.

In adjust registration step 220 the processor uses the image generated by camera 72 to determine 3D coordinate values, in the optical frame of reference of marker 66, of distal tip 238 and verification point 108. There is a difference in these coordinate values, illustrated by the negative return of decision step 218, corresponding to a gap between the two values. The processor then adjusts the registrations performed in steps 206 and 208 in order to reduce the gap and returns, iteratively, to decision step 218. The iterations of decision step 218 and adjustment step 220 continue until decision step 218 returns positive.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Apparatus, comprising:
   a hinge, defining a hinge axis;
   a pair of opposing jaws terminating at respective proximal regions and distal regions, wherein the proximal regions are connected to the hinge so that at least one of the jaws is configured to rotate about the hinge between a closed state and an open state of the jaws, and the jaws are curved in respective planes parallel to the hinge axis, and terminate in respective narrowed ends at the respective distal regions, wherein in the closed state the jaws are configured to grip at least two sections of vertebrae;

a support structure, configured to retain the hinge and the pair of opposing jaws; and a multiplicity of pyramid-like sharp teeth disposed on respective inner surfaces of the opposing jaws, wherein the support structure comprises a lever mechanism, actuated by a set screw retained by an open aperture in the support structure, attached to the proximal region of the at least one of the jaws, the mechanism having a first configuration fixedly maintaining the jaws in the open state, and a second configuration fixedly maintaining the jaws in the closed state.

2. The apparatus according to claim 1, wherein the pair of opposing jaws comprises a jaw fixed with respect to the hinge, the apparatus further comprising a verification point located in a fixed position within an element of the apparatus consisting of one of the fixed jaw and the support structure, wherein the verification point is identifiable in a fluoroscopic image of the element and is visible when illuminated by visible light and when the jaws grip the at least two sections of the vertebrae.

3. The apparatus according to claim 1, and comprising a detachable positioning marker, configured to be fixedly and rigidly attached in one of a plurality of positions to the support structure.

4. The apparatus according to claim 3, and comprising a surgical navigation system, an image capturing device therein, and a processor, wherein the surgical navigation system is remote from the positioning marker, and wherein the image capturing device is configured to capture an image of the marker and wherein the processor is configured to analyze the image so as determine the position and orientation of the marker in a frame of reference defined by the system.

5. The apparatus according to claim 1, wherein each of the sharp teeth terminates in a sharp point.

6. The apparatus according to claim 1, wherein each of the sharp teeth comprises a proximally-facing sharp edge.

7. The apparatus according to claim 1, wherein each of the sharp teeth comprises a distally-facing sharp edge.

8. The apparatus according to claim 1, wherein the respective proximal regions and distal regions comprise straight regions connected by a curved intermediate section.

9. The apparatus according to claim 8, wherein an angle between the straight sections is in a range from 70°-90°.

10. The apparatus according to claim 1, wherein the respective narrowed ends are rounded and truncated.

11. The apparatus according to claim 1, wherein the jaws are configured so that when the jaws grip the one or more sections of the vertebrae the jaws bend so that respective distal terminations of the distal regions deflect by up to 1 mm.

12. A method, comprising:
providing a clamp, comprising:
a hinge, defining a hinge axis;
a pair of opposing jaws, each jaw terminating at respective proximal regions and distal regions, wherein the proximal regions are connected to the hinge so that at least one of the jaws is configured to rotate about the hinge between a closed state and an open state of the jaws, and the jaws are curved in respective planes parallel to the hinge axis, and terminate in respective narrowed regions at the respective distal regions, wherein in the closed state the jaws are configured to grip at least two sections of vertebrae;
a support structure, configured to retain the hinge and the pair of opposing jaws;
a multiplicity of pyramid-like sharp teeth disposed on respective inner surfaces of the opposing jaws; and
a detachable positioning marker, configured to be fixedly and rigidly attached in one of a plurality of positions to the support structure; and
using the clamp during an image guided surgery procedure,
wherein the support structure comprises a lever mechanism, actuated by a set screw retained by an open aperture in the support structure, attached to the proximal region of the at least one of the jaws, the mechanism having a first configuration fixedly maintaining the jaws in the open state, and a second configuration fixedly maintaining the jaws in the closed state.

13. The method according to claim 12, wherein the pair of opposing jaws comprises a jaw fixed with respect to the hinge, the method further comprising locating a verification point in a fixed position within an element consisting of one of the fixed jaw and the support structure, wherein the verification point is identifiable in a fluoroscopic image of the element and is visible when illuminated by visible light.

14. The method according to claim 12, and comprising providing a surgical navigation system, an image capturing device therein, and a processor, wherein the surgical navigation system is remote from the positioning marker, and wherein the image capturing device is configured to capture an image of the marker and wherein the processor is configured to analyze the image so as determine the position and orientation of the marker in a frame of reference defined by the system.

15. The method according to claim 12, wherein each of the sharp teeth terminates in a sharp point.

16. The method according to claim 12, wherein each of the sharp teeth comprises a proximally-facing sharp edge.

17. The method according to claim 12, wherein each of the sharp teeth comprises a distally-facing sharp edge.

18. The method according to claim 12, wherein the respective proximal regions and distal regions comprise straight regions connected by a curved intermediate section.

19. The method according to claim 12, wherein the respective narrowed ends are rounded and truncated.

20. The method according to claim 12, wherein the jaws are configured so that when the jaws grip the one or more sections of the vertebrae the jaws bend so that the distal regions deflect by up to 1 mm.

* * * * *